United States Patent [19]
Saunders

[11] Patent Number: 4,468,821
[45] Date of Patent: Sep. 4, 1984

[54] PNEUMATIC LEG STIFFENER

[75] Inventor: Gerald Saunders, Sydenham, Canada

[73] Assignee: Queen's University at Kingston, Kingston, Canada

[21] Appl. No.: 473,251

[22] Filed: Mar. 9, 1983

[51] Int. Cl.³ .......................... A61F 1/02; A61F 1/08; A61F 1/12
[52] U.S. Cl. .............................................. 3/18; 3/20; 128/DIG. 20
[58] Field of Search ........................................ 3/17–21, 3/2; 128/DIG. 20, 87 R, 89

[56] References Cited

U.S. PATENT DOCUMENTS

| | | | |
|---|---|---|---|
| 2,823,668 | 2/1958 | Van Court et al. | 128/DIG. 20 |
| 3,889,301 | 6/1975 | Bonner, Sr. | 3/20 |
| 4,128,903 | 12/1978 | Marsh et al. | 3/19 |
| 4,300,245 | 11/1981 | Saunders | 3/20 X |

Primary Examiner—Ronald L. Frinks
Attorney, Agent, or Firm—Richard J. Hicks; Stanley E. Johnson

[57] ABSTRACT

An artificial limb consisting of a tubular member having inner and outer walls and formed by at least three interconnected side-by-side air inflatable compartments fabricated from an air impervious flexible material. The stump of a patient's limb may be inserted into one end of the tubular member, which preferably tapers therefrom towards the other end, and is gripped by the inner walls thereof when the compartments are inflated. Below the stump the inner walls interengage with one another as the compartments inflate and in order to provide a sufficiently rigid pylon to fully support the patient's weight a plurality of rigid longitudinal stiffening members are disposed around, and cooperate with, the outer walls of the tubular member. Preferably the stiffening members are hingedly interconnected along longitudinal marginal side edges and fabricated from a single sheet of rigid transparent thermoplastic material such as polyvinylchloride.

5 Claims, 7 Drawing Figures

PNEUMATIC LEG STIFFENER

BACKGROUND OF INVENTION

This invention relates generally to artificial limbs and more particularly to an inflatable artificial leg of the type described in more detail in my prior Canadian Pat. No. 1,132,754 issued Oct. 5, 1982 and its counterpart U.S. Pat. No. 4,300,245 issued Nov. 17, 1981 for Pneumatic Leg.

In my prior patent there is described an artificial limb comprising a tubular double walled member having an inner and outer wall both made of a flexible, preferably transparent, thermoplastics material and sealed together at each end and along three longitudinal lines so as to form three side-by-side inflatable compartments along the length of the tube. The tubular member tapers from one end to the other and provision is made for insertion of the stump of a limb at the thick end, and for the inner walls of the three compartments to interengage along their length, when inflated, so as to provide a relatively stiff pylon which resists buckling when supporting at least a portion of the patient's weight. Such an artificial leg is particularly useful immediately after amputation surgery or after extended use of a conventional prosthesis. It is light, comfortable and easy to put on. If transparent, examination of the stump after surgery can be made without removing the artificial limb of the present invention. It will be appreciated that the leg of the present invention is particularly useful to control swelling after amputation and it is of particular convenience not to have to remove it for examination of the stump. While the artificial leg of my prior invention has achieved some considerable success as an initial after surgery prosthesis it has not been as entirely successful, as originally intended, as a general use prosthesis, despite its light weight and comfort, as the weight bearing capacity without buckling has proved to be somewhat limited. In the case of a large or heavy patient it has not always proved possible to reliably support all of the patient's weight.

OBJECT OF INVENTION

It is therefore an object of the present invention to provide means for stiffening the pneumatic leg of my prior invention so that it will reliably support all of a patient's weight.

Thus, by one aspect of this invention there is provided in an artificial limb comprising a plurality of side-by-side air inflatable, intercommunicating compartments fabricated from a flexible air impervious material and extending along the entire length of said limb and having air passage inlet means into one of said compartments for use in inflation of said compartments, arranged to provide a tubular member having inner and outer walls, open at one end thereof to receive the stump of a patient's limb therein and tapered towards the other end thereof and wherein the inner walls of the compartments are in interengagement with each other from the stump of the limb to the other end when the compartments are inflated, the improvement comprising a plurality of substantially rigid longitudinally extending stiffening members arranged around the outer walls of said tubular member and cooperating therewith when said compartments are inflated so as to provide a relatively stiff pylon member which resists buckling when supporting the patient's weight.

DETAILED DESCRIPTION OF PREFERRED EMBODIMENTS

Figure 1:
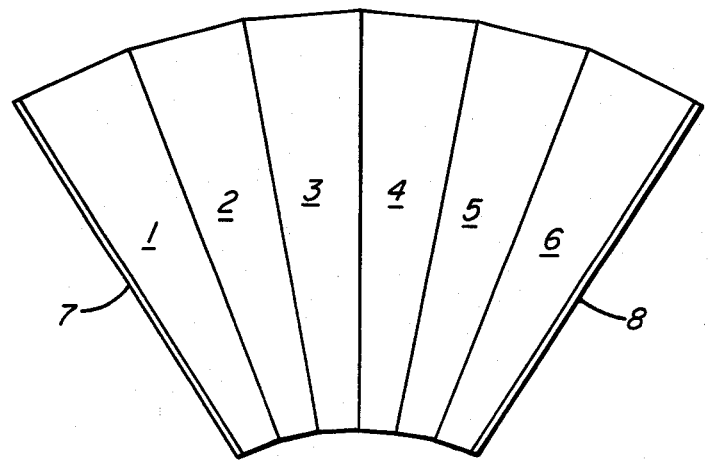
FIG. 1 is a side elevational view of the stiffener of the present invention in an open position.
Figure 2:
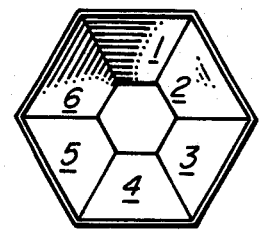
FIG. 2 is a top plan view of the stiffener of FIG. 1 in closed position.
Figure 3:
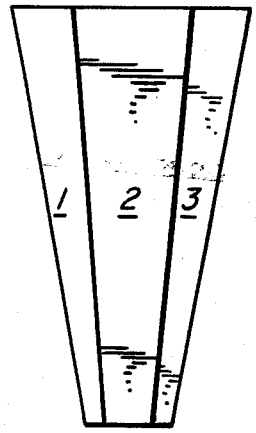
FIG. 3 is a side view of the stiffener of FIG. 1 in closed position.
Figure 4:
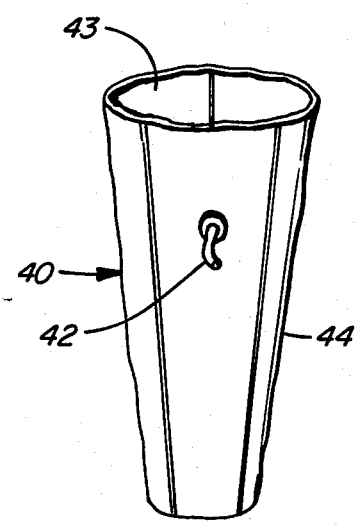
FIG. 4 is a side view of an air leg according to the prior art.
Figure 5:
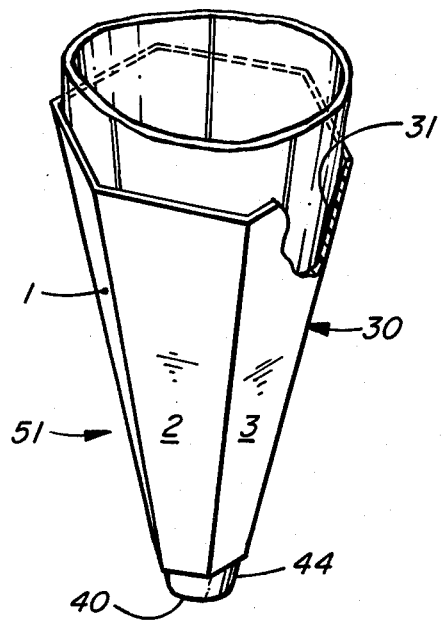
FIG. 5 is a side view of the stiffener of FIGS. 1, 2 and 3 in operative position on an air leg of FIG. 4.

As seen in FIG. 1, the stiffener of the present invention comprises six substantially rigid, transparent panels 1, 2, 3, 4, 5, 6 which are substantially rectangular in shape and longitudinally tapered. The six panels are arranged in longitudinal side-by-side relation and joined together along adjacent marginal side edges thereof. The free longitudinal edges 7, 8 of panels 1 and 6 respectively are arranged to be releasably secured together by any conventional means such as interengaging integrally formed hooked members, press studs or the like. Preferably, but not essentially, panels 1-6 are fabricated from a single sheet of substantially rigid, transparent thermoplastics material such as P.V.C., $\frac{1}{8}$-$\frac{1}{4}$" thick, having weakened fold or bend lines formed therein by heating to form the adjacent marginal side edges of the panels 1-6. When edges 7, 8 are interengaged a relatively unstable tapered tubelike structure 30 is produced, as shown in FIGS. 2 and 3, but dimensioned to surround a partially inflated air leg 40 of my prior invention (FIG. 4). FIG. 4 shows an air leg 40 of my prior patent, comprising at least three side-by-side longitudinal compartments which are in fluid communication with each other and inflatable by means of an air inlet 42 in one of the compartments. Preferably the air leg is slightly tapered towards the bottom. A patient's stump 43 (shown in phantom in FIG. 4) can be inserted into the top of the air leg 40 where it is gripped and held under slight compression by the inner faces of the inflated compartments. Below stump 43, the inner faces of the three compartments come into interengagement with each other to provide a relatively stiff pylon which is capable of supporting at least a portion of the patient's weight. Upon complete inflation of air leg 40, as shown in FIG. 5 by means of air inlet means 42, the peripheral surface 44 thereof engages the inner surface 31 of the tube 30 to form a composite, longitudinally rigid pylon 51 which is stiff enough to support the entire weight of even a relatively heavy patient.

Figure 6:
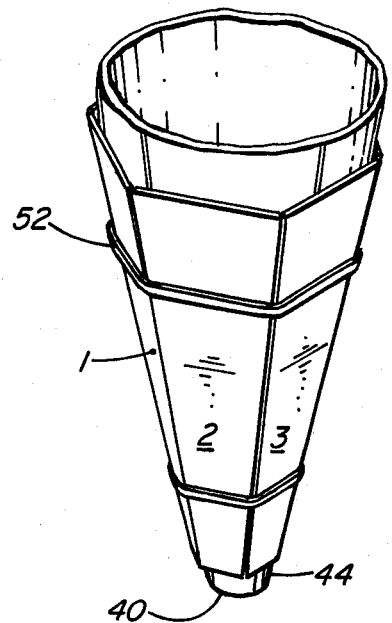
FIG. 6 is a side view of an alternative embodiment of the stiffener in operative position on an air leg of FIG. 4.
Figure 7:
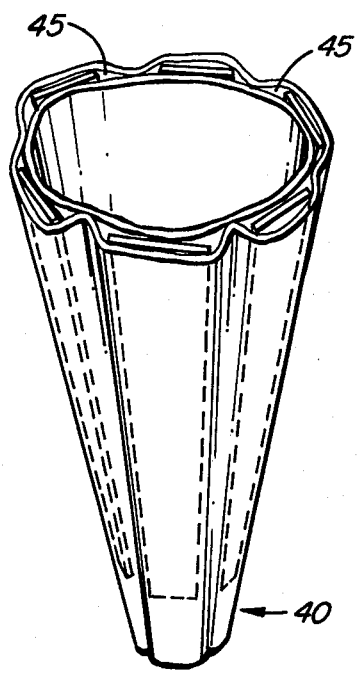
FIG. 7 is a side view of a second alternative embodiment of the stiffener in operative position on a modified air leg of FIG. 4.

It will, of course, be appreciated that the stiffening elements 1-6 of the present invention need not be integrally formed or interconnected but may be individually secured around an air leg 40 by external securing means such as straps 52, Velcro ® fasteners or the like as shown in FIG. 6. In yet another embodiment, a plurality of transparent, rigid, stiffening elements 1-6 may be disposed circumferentially around an air leg 40 in a series of pockets 45 formed integrally therewith, as shown in FIG. 7.

I claim:

1. In an artificial limb comprising a plurality of side-by-side air inflatable, intercommunicating compartments fabricated from a flexible air impervious material and extending along the entire length of said limb and having air passage inlet means into one of said compartments for use in inflation of said compartments, arranged to provide a tubular member having inner and outer walls, open at one end thereof to receive the stump of a patient's limb therein and tapered towards the other end thereof and wherein the inner walls of the compartments are in inter-engagement with each other from the stump of the limb to the other end when the compartments are inflated, the improvement comprising a plurality of substantially rigid, longitudinally extending stiffening members hingedly interconnected along adjacent marginal side edges thereof to form an outer tubular member supporting the outer walls of said tubular member and cooperating therewith when said compartments are inflated so as to provide a relatively stiff pylon member which resists buckling when supporting the patient's weight.

2. An artificial limb as claimed in claim 1 wherein said stiffening members are integrally formed from a sheet of substantially rigid thermoplastics material.

3. An artificial limb as claimed in claim 1 wherein said tubular member and rigid stiffening members are fabricated from substantially transparent materials.

4. In an artificial limb comprising a plurality of side-by-side air inflatable, intercommunicating compartments fabricated from a flexible air impervious material and extending along the entire length of said limb and having air passage inlet means into one of said compartments for use in inflation of said compartments, arranged to provide a tubular member having inner and outer walls, open at one end thereof to receive the stump of a patient's limb therein and tapered towards the other end thereof and wherein the inner walls of the compartments are in interengagement with each other from the stump of the limb to the other end when the compartments are inflated, the improvement comprising a plurality of substantially rigid longitudinally extending, separate stiffening members arranged circumferentially and longitudinally around said outer walls in respective ones of a plurality of pockets in said outer walls each arranged to receive a stiffening member, so as to provide, when said compartments are inflated, a relatively stiff pylon member which resists buckling when supporting the patient's weight.

5. An aritificial limb as claimed in claim 4 wherein said tubular member and rigid stiffening members are fabricated from substantially transparent materials.

* * * * *